United States Patent
Grashow et al.

(10) Patent No.: US 11,458,268 B2
(45) Date of Patent: Oct. 4, 2022

(54) SYSTEMS AND METHODS FOR CONCURRENT AIRWAY STABILIZATION AND PULMONARY STRETCH RECEPTOR ACTIVATION

(71) Applicant: KONINKLIJKE PHILIPS N.V., Eindhoven (NL)

(72) Inventors: Jonathan Sayer Grashow, Cheswick, PA (US); Gregory Delano Matthews, Pittsburgh, PA (US); Michael Thomas Kane, Harrison City, PA (US); Eugene Nelson Scarberry, Trafford, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 351 days.

(21) Appl. No.: 16/492,678

(22) PCT Filed: Mar. 23, 2018

(86) PCT No.: PCT/EP2018/057410
§ 371 (c)(1),
(2) Date: Sep. 10, 2019

(87) PCT Pub. No.: WO2018/177913
PCT Pub. Date: Oct. 4, 2018

(65) Prior Publication Data
US 2020/0046925 A1 Feb. 13, 2020

Related U.S. Application Data

(60) Provisional application No. 62/479,886, filed on Mar. 31, 2017.

(51) Int. Cl.
*A61M 16/00* (2006.01)

(52) U.S. Cl.
CPC ...... *A61M 16/024* (2017.08); *A61M 16/0066* (2013.01); *A61M 2016/003* (2013.01);
(Continued)

(58) Field of Classification Search
CPC .............. A61M 16/00; A61M 16/0051; A61M 16/0066; A61M 16/022; A61M 16/024;
(Continued)

(56) References Cited

U.S. PATENT DOCUMENTS 5,148,802 A 9/1992 Sanders
5,313,937 A 5/1994 Zdrojkowski
(Continued)

FOREIGN PATENT DOCUMENTS

WO 2012085748 A1 6/2012

OTHER PUBLICATIONS

Relu Cernes, MD. and Reuven Zimlichman, MD, "Resperate: the Role of Paced Breathing in Hypertension Treatment", Journal of American Society of Hypertension 9(1) (2015) 38-47.
(Continued)

*Primary Examiner* — Joseph D. Boecker

(57) ABSTRACT

A method for the concurrent treatment of obstructive sleep apnea and hypertension in a patient comprises providing a flow of treatment gas to the airway of the patient in accordance with a first set of flow parameters. Determining that the patient has achieved stable breathing while receiving the provided flow of treatment gas in accordance with the first set of parameters. Determining a set of target patient breath parameters from breath data collected from the patient. Adjusting the flow of treatment gas to a different set of flow parameters. Determining that the new patient breath data, collected from the patient, accords with the target patient breath parameters and providing the flow of treatment gas to the patient in accordance with the different set of flow (Continued)

parameters. The target patient breath parameters include a target tidal volume of the patient which is greater than a first tidal volume of the patient.

20 Claims, 3 Drawing Sheets

(52) U.S. Cl.
CPC . *A61M 2016/0027* (2013.01); *A61M 2205/50* (2013.01); *A61M 2230/40* (2013.01); *A61M 2230/46* (2013.01)

(58) Field of Classification Search
CPC .... A61M 2016/0027; A61M 2016/003; A61M 2016/0033; A61M 2016/0036; A61M 2016/0039; A61M 2230/40; A61M 2230/46
See application file for complete search history.

(56) References Cited

U.S. PATENT DOCUMENTS

| | | | |
|---|---|---|---|
| 5,433,193 A | 7/1995 | Sanders | |
| 5,632,269 A | 5/1997 | Zdrojkowski | |
| 5,800,337 A | 9/1998 | Gavish | |
| 5,803,065 A | 9/1998 | Zdrojkowski | |
| 6,029,664 A | 2/2000 | Zdrojkowski | |
| 6,539,940 B2 | 4/2003 | Zdrojkowski | |
| 6,626,175 B2 | 9/2003 | Jafari | |
| 7,011,091 B2 | 3/2006 | Hill | |
| 9,205,210 B2* | 12/2015 | Bassin | A61M 16/022 |
| 2007/0169776 A1 | 7/2007 | Kepler | |
| 2012/0003620 A1* | 1/2012 | Pittman | A63B 23/0244 |
| | | | 434/262 |
| 2012/0097155 A1* | 4/2012 | Iyer | A61M 11/00 |
| | | | 128/200.14 |
| 2012/0291784 A1* | 11/2012 | Robinson | A61M 16/0051 |
| | | | 128/204.23 |
| 2012/0298108 A1* | 11/2012 | Kane | A61M 16/0066 |
| | | | 128/204.23 |

OTHER PUBLICATIONS

Chacko N. Joseph, Cesare Porta, Gaia Casucci, Nadia Casiraghi, Mara Maffeis, Marco Rossi, Luciano Bernardi, "Slow Breathing Improves Arterial Baroreflex Sensitivity ADN Decreases Blood Pressure in Essential Hypertension", pp. 1-5.
Edward S. Schelegle, Jerry F. Green, "An Overview of the Anatomy and Physiology of Slowly Adapting Pulmonary Stretch Receptors", Respiration Physiology 125 (2001) 17-31.
International Search Report dated Jun. 28, 2018.

* cited by examiner

SYSTEMS AND METHODS FOR CONCURRENT AIRWAY STABILIZATION AND PULMONARY STRETCH RECEPTOR ACTIVATION

This application is the U.S. National Phase application under 35 U.S.C. § 371 of International Application No. PCT/EP2018/057410, filed on Mar. 23, 2018 and U.S. Provisional Application No. 62/479,886 filed Mar. 31, 2017. These applications are hereby incorporated by reference herein.

BACKGROUND OF THE INVENTION

1. Field of the Invention

The present invention pertains systems for delivering a pressurized flow of treatment gas to the airway of a patient, and, in particular to system for concurrently stabilizing the airway of a patient and activating pulmonary stretch receptors of the patient in order to lower blood pressure. The present invention also pertains to methods for concurrently stabilizing an airway of a patient and activating pulmonary stretch receptors of the patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Hypertension is a significant problem in nearly all western cultures and is an underlying cause for stroke and heart attack. Termed the "Silent Killer," hypertension affects approximately 1 in 4 Americans, and occurs with even higher prevalence in some European communities. Hypertension is also gaining recognition as a co-morbid factor in obstructed sleep apnea (OSA) patient populations, with recent studies indicating that as many as 80% of patients seeking treatment for OSA may unknowingly suffer from this disease.

Slower breathing has been shown to effectively reduce hypertension. Indeed, a focus of techniques such as Yoga and Qigong is to slow a person's breathing to effectively relieve stress and lower blood pressure. In recent years, the physiological mechanisms underlying this response have been shown to involve changes in the autonomic nervous system through the following chain of events: The process of slow breathing requires the autonomic nervous system to make more frequent adjustments in blood pressure. In response to these frequent changes, the autonomic nervous system becomes more sensitive to blood pressure (BP) changes (via the baroreflex). The baroreflex becomes amplified. In order to better regulate BP, a readjustment of central neural control occurs by increasing vagal activity and inhibiting sympathetic activity, both of which act to reduce BP.

Several studies support the idea of using slower breathing to reduce blood pressure in hypertensive individuals. Currently, one device on the market (RESPeRATE™ by Intercure™ (Fort Lee, N.J.)) is FDA approved for the treatment of hypertension. The RESPeRATE™ device is designed to act as a breathing "coach" by using audiovisual cues to guide the user to a slower breath rate.

The operation of this device is described, at least in part, in U.S. Pat. No. 5,800,337 to Gavish. Gavish discloses a system for modifying naturally occurring biorhythmic activity by changing at least one "non-frequency" characteristic of input to the user in response to changes in the biorhythmic activity of the user. A focus of Gavish is to effect absolute and relative durations of portions or segments of an overall biorhythmic pattern, such as breathing, independently of changes in the overall frequency of the user's biorhythm being monitored (again, e.g., breathing). The input to the user that is disclosed by Gavish includes audio, visual or tactile cues. While such treatment has been shown to be effective when properly carried out, patients commonly have difficulty complying with the therapy as the deep breathing exercises often trigger sleep onset before an adequate therapy period has been completed. Additionally, the equipment needed to provide the necessary inputs to the user can be annoyance for the patient.

While still other biorhythmic feedback methodologies are known, there is nevertheless a need for different approaches to effect the breathing of a patient to induce, among other things, lower blood pressure, or simply induce improved periods of relaxation.

SUMMARY OF THE INVENTION

Accordingly, it is an object of the present invention to provide a system and method that overcomes the shortcomings of conventional. As one aspect of the invention, a method for the concurrent treatment of obstructive sleep apnea and hypertension in a patient is provided. The method comprises: providing a flow of treatment gas to the airway of the patient in accordance with a first set of flow parameters; determining that the patient has achieved stable breathing while receiving the provided flow of treatment gas in accordance with the first set of parameters; collecting breath data of the patient while receiving the flow of treatment gas in accordance with the first set of parameters; determining a set of target patient breath parameters from the breath data; adjusting the flow of treatment gas to a different set of flow parameters; monitoring the patient to obtain new patient breath data; determining that the new patient breath data accords with the target patient breath parameters; and providing the flow of treatment gas to the patient in accordance with the different set of flow parameters, wherein the target patient breath parameters include a target tidal volume of the patient which is greater than a first tidal volume of the patient.

The target tidal volume is in the range of about 150% to about 400% of the first tidal volume.

Determining that the patient has achieved stable breathing may comprise determining that at least one of a minute ventilation, a breath rate, or a tidal volume of the patient is consistent.

Collecting breath data may comprise determining at least one of a minute ventilation, a breath rate, or a tidal volume of the patient.

Adjusting the flow of treatment gas to bring the patient breath data into accordance with the target patient breath parameters may be carried out gradually over a predetermined period of time.

Adjusting the flow of treatment gas to bring the patient breath data into accordance with the target patient breath parameters may be carried out over a predetermined quantity of breaths by the patient.

The method may further comprise determining that a stop condition has occurred, and responsive thereto, providing the flow of breathing gas in accordance with the first set of parameters.

Determining that a stop condition has occurred may comprise determining that a breath tail of the patient exceeds a predetermined length of time.

Determining that a stop condition has occurred may comprise determining that a breathing instability has occurred.

Determining that a stop condition has occurred may comprise determining a change in lung compliance.

Determining that a stop condition has occurred may comprise determining that a predetermined amount of time has passed.

The method may further comprise: determining that the stop condition has ceased; determining that the patient has achieved stable breathing; and again providing the flow of treatment gas to the patient in accordance with the different set of flow parameters.

As another aspect of the invention, a gas flow generator having a controller which is programmed to carry out the methods described herein is provided.

As yet another aspect of the invention, a machine readable memory having instructions encoded therein for carrying out the methods described herein is provided.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
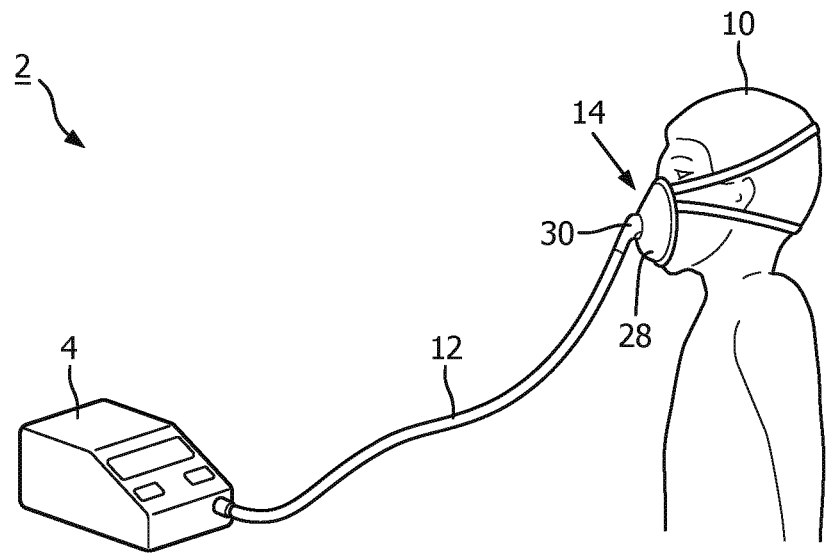
FIG. 1 is a schematic diagram showing an airway pressure support system according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, "minute ventilation" or "MV" for short, refers to the volume of air breathed by a patient in a minute.

As used herein, "breath rate" or "BR" for short, refers to quantity of breaths a patient takes in a minute.

As used herein, "tidal volume" or "TV" for short, refers to the volume of air displaced by a patient during one of an inhalation or an exhalation.

As used herein, "lung compliance" or "LC" for short, refers generally to the stiffness of the patient's lungs.

As used herein, a breath "tail" of a patient, refers to the time between an exhalation and a subsequent inhalation by the patient.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Pulmonary stretch receptors are afferent nerve endings located throughout the airway (trachea, bronchi, and bronchioles). These nerve endings are attached to smooth muscle, collagen, and elastin fibers in the tissue membranes. Pulmonary stretch receptors are activated when the tissue is stretched, but slowly deactivate if the stretch is maintained. During normal breathing, these receptors are activated to some degree during each inspiration since the tissue is stretched/un-stretched cyclically over the course of each breath cycle. Stretching these receptors beyond the threshold of a typical breath (e.g., by inflating the lung by an additional 50-300% of nominal tidal volume) triggers a reflex, governed by the autonomic nervous system, to dilate peripheral blood vessels, which results in reduced blood pressure, especially in hypertensive patients. Embodiments of the present invention utilize such receptors to simultaneously and effectively treat both obstructive sleep apnea (OSA) and hypertension.

Figure 2:
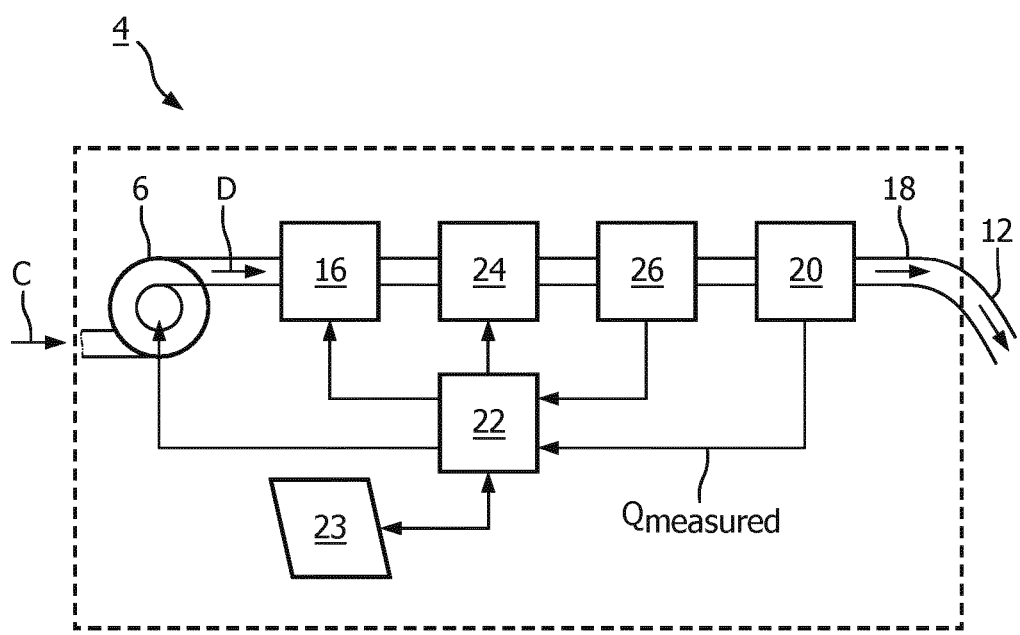
FIG. 2 is a schematic diagram of the pressure generating device of the pressure support system of FIG. 1.

FIG. 1 shows a schematic diagram of an airway pressure support system 2 according to one particular, non-limiting exemplary embodiment of the present invention. Airway pressure support system 2 includes a pressure generating device 4, a schematic diagram of which is shown in FIG. 2. Referring to FIGS. 1 and 2, pressure generating device 4 includes a gas flow generator 6, such as a blower used in a conventional CPAP or bi-level pressure support device. Gas flow generator 6 receives breathing gas, generally indicated by arrow C, from the ambient atmosphere and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cm H2O. The pressurized flow of breathing gas from gas flow generator 6, generally indicated by arrow D, is delivered via a delivery conduit 12 to a patient interface device 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 2 shown in FIG. 1 is what is known as a single-limb system, meaning that the patient circuit includes only delivery conduit 12 connecting patient 10 to pressure support system 2. As such, an exhaust vent (not numbered) is provided in patient interface device 14 for venting exhaled gases from the system. It should be noted that the exhaust vent can be provided at other locations in addition to or instead of in patient interface device 14, such as in delivery conduit 12. It should also be understood that the exhaust vent can have a wide variety of configurations depending on the desired manner in which gas is to be vented from pressure support system 2.

The present invention also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

In the illustrated embodiment, pressure generating device 4 includes a pressure controller in the form of a valve 16 provided in an internal delivery conduit 18 provided in pressure generating device 4. Valve 16 controls the pressure of the flow of breathing gas from gas flow generator 6 that is delivered to patient 10. For present purposes, gas flow generator 6 and valve 16 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 16 is optional depending on the technique used to control the pressure of the flow of breathing gas delivered to patient 10. If valve 16 is eliminated, the pressure generating system corresponds to gas flow generator 6 alone, and the pressure of gas in the patient circuit is controlled, for example, by controlling the motor speed of gas flow generator 6.

Pressure generating device 4 further includes a flow sensor 20 that measures the flow of the breathing gas within delivery conduit 18 and delivery conduit 12. In the particular embodiment shown in FIG. 2, flow sensor 20 is interposed in line with delivery conduits 18 and 12, most preferably downstream of valve 16. Flow sensor 20 generates a flow signal, $Q_{MEASURED}$, that is provided to a controller 22 and is used by controller 22 to determine the flow of gas at patient 10 ($Q_{PATIENT}$).

Techniques for calculating $Q_{PATIENT}$ based on $Q_{MEASURED}$ are well known, and take into consideration the pressure drop of the patient circuit, known leaks from the system, i.e., the intentional exhausting of gas from the circuit as described herein, and unknown (unintentional) leaks from the system, such as leaks at the mask/patient interface. The present invention contemplates using any known or hereafter developed technique for calculating total leak flow $Q_{LEAK}$, and using this determination in calculating $Q_{PATIENT}$ based on $Q_{MEASURED}$ (and for other purposes as described elsewhere herein). Examples of such techniques are taught by U.S. Pat. Nos. 5,148,802; 5,313,937; 5,433,193; 5,632, 269; 5,803,065; 6,029,664; 6,539,940; 6,626,175; and 7,011, 091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 16.

Controller 22 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2.

An input/output device 23 is provided for setting various parameters used by airway pressure support system 2, as well as for displaying and outputting information and data to a user, such as a clinician or caregiver.

Furthermore, in the illustrated embodiment, pressure generating device 4 also includes a humidifier 24. Alternatively, humidifier 24 may be separate from and located external to pressure generating device 4. Humidifier 24 is controlled by controller 22. Humidifier 24 further improves comfort by providing moisture in the supplied gas. In the exemplary embodiment, humidifier 24 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

Pressure generating device 4 also includes a pressure sensor 26 that measures the pressure of the breathing gas within delivery conduit 18 and delivery conduit 12. In the particular embodiment shown in FIG. 2, pressure sensor 26 is interposed in line with delivery conduits 18 and 12, downstream of valve 16. Pressure sensor 26 generates a pressure signal (not labeled), that is provided to controller 22 and is used by controller 22 in carrying out the methods described further herein.

In the exemplary embodiment, patient interface device 14 includes a patient sealing assembly 28, which in the illustrated embodiment is a full face mask. However, other types of patient interface devices, such as, without limitation, a nasal mask, a nasal/oral mask, or a nasal cushion, which facilitate the delivery of the flow of breathing gas to the airway of a patient may be substituted for patient sealing assembly 28 while remaining within the scope of the present invention. A fluid coupling conduit 30 having an exhaust vent (not numbered) is coupled to an opening in patient sealing assembly 28 to allow the flow of breathing gas from pressure generating device 4 to be communicated to an interior space defined by patient sealing assembly 28, and then to the airway of a patient. Patient interface device 14 also includes a headgear component 32 for securing patient sealing assembly 28 to the head of patient 10. It will be understood that the patient interface device 14 described herein is meant to be exemplary only, and that other arrangements are also possible without varying from the scope of the present invention.

In the illustrated, non-limiting exemplary embodiment of the present invention, airway pressure support system 2 essentially functions as a CPAP pressure support system, and, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 3I:
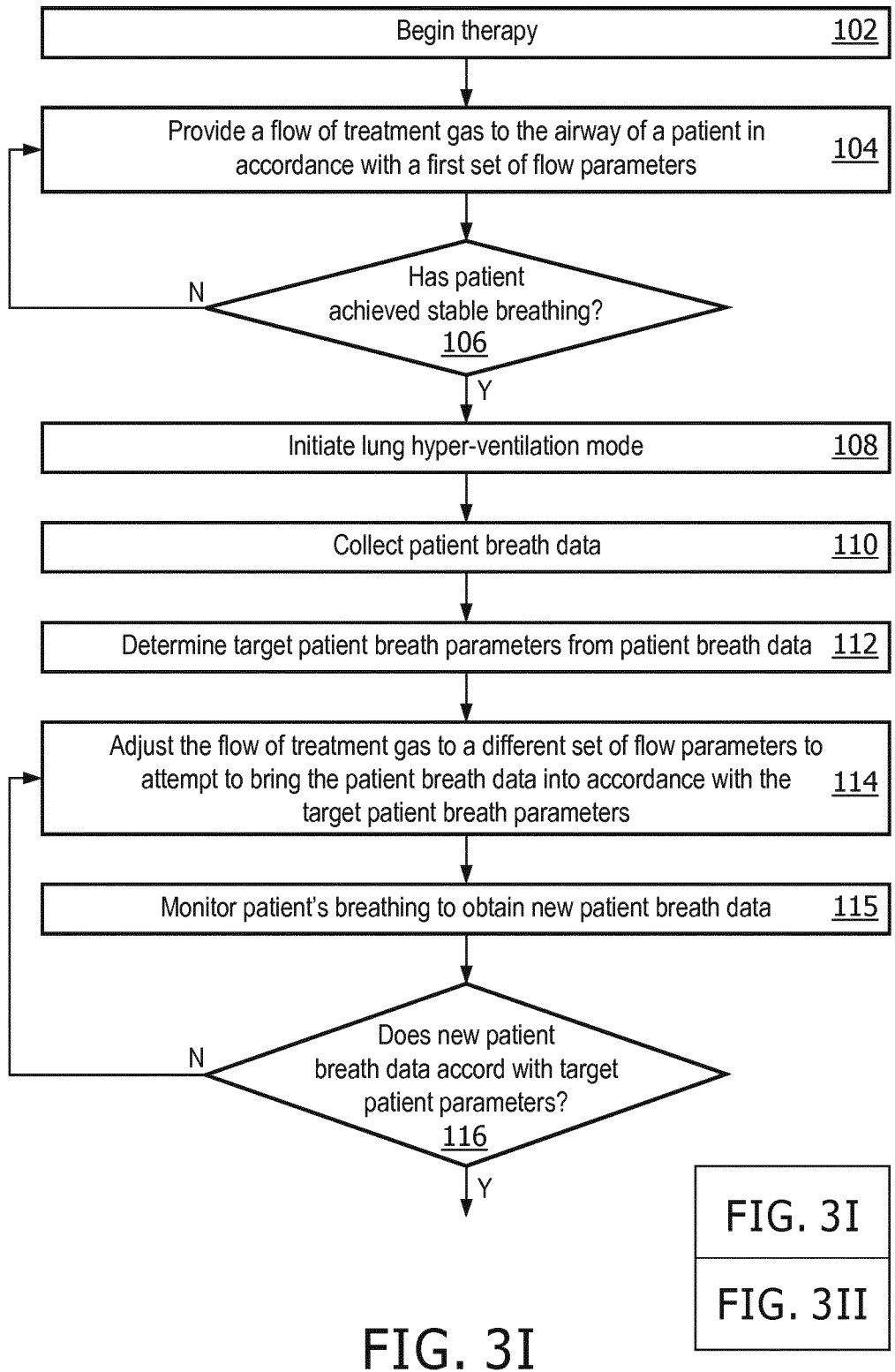
FIG. 3 is a flowchart showing a method for concurrently stabilizing the airway of a patient and treating hypertension according to an exemplary embodiment of the present invention.
Figure 3I:
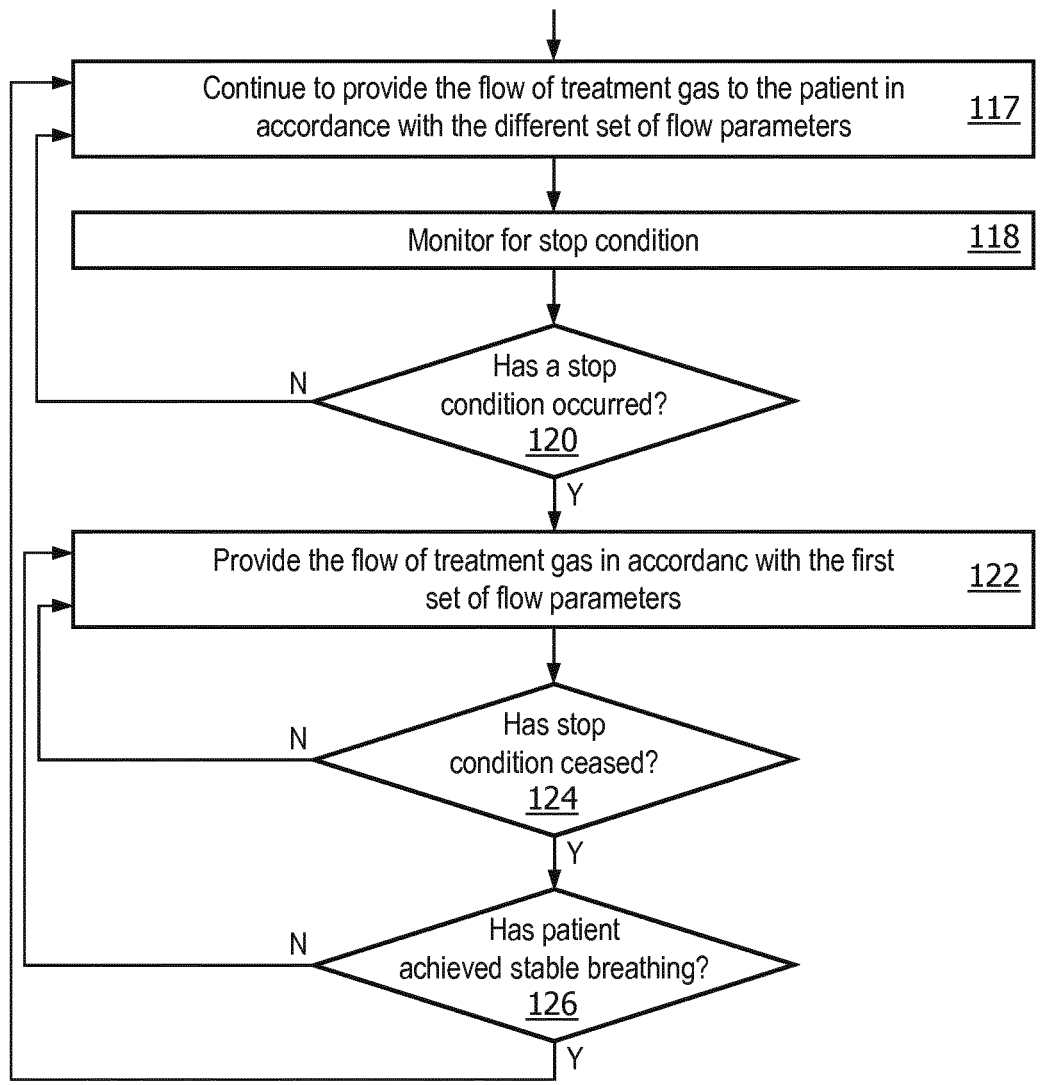

FIG. 3 is a flowchart showing a method 100 that may be implemented in conjunction with pressure support system 2 for concurrently stabilizing the airway of patient 10 (e.g., without limitation, such as for treating OSA) while also treating hypertension. Method 100 begins at step 102, when patient 10 begins their CPAP therapy such as by securing patient interface device 14 on their head and powering up/starting pressure generating device 4. Next, as shown at step 104, a flow of treatment gas is provided (e.g., via pressure generating device 4 of FIG. 1) to the patient in accordance with a first set of flow parameters. In an example embodiment utilizing the system 2 such as shown in FIG. 1, pressure generating device 4 is operated in a "default CPAP mode". If auto titrating, then EPAP is adjusted by pressure generating device 4 as needed until airway patency is achieved. As shown in step 106, the flow of breathing gas is provided in accordance with the first set of flow parameters (e.g., in default CPAP mode) until it is determined that the patient has achieved stable breathing. Such determination may be made by considering one or more of several characteristics of the patient's breathing. For example, consistent minute ventilation (MV), breath rate (BR), tidal volume (TV), and/or lung compliance may be used to indicate that stable breathing has been achieved. It is to be appreciated that mechanisms and methods for determining and analyzing such characteristics are well known in the art and may be utilized without varying from the scope of the present invention. Accordingly, a detailed description of such mechanisms/techniques has not been provided herein.

Once it is determined at step 106 that the patient has achieved stable breathing, the method moves on to step 108 where lung hyper-ventilation mode is initiated. Next, as an initial step of hyper-ventilation mode, breath data (e.g., MV, BR, TV, LC) is collected at step 110 from which target patient breath parameters are then calculated, such as shown at step 112. As previously discussed, in order to effectively activate the patient's pulmonary stretch receptors, the patient's lungs generally need to be inflated beyond the threshold of a typical breath. Accordingly, the target patient breath parameters aim to inflate the lungs of the patient by an additional 50-400% of nominal tidal volume. For example, in one embodiment in which target TV is 200% of baseline TV, the target BR is approximately 50% of the baseline BR, so as to generally maintain the patient's MV. The collection of patient breath data at step 110 typically occurs over a few minutes, although such time may be varied without varying from the scope of the present invention. It is to be appreciated that mechanisms and methods for collecting and analyzing patient breath data (e.g., via pressure generating device 4) are well known in the art and may be utilized without varying from the scope of the present invention. Accordingly, a detailed description of such mechanisms/techniques has not been provided herein.

After the patient breath data has been collected at step 110 and target patient breath parameters are calculated/determined therefrom at step 112, the flow of breathing gas (e.g., the inspiratory positive airway pressure (IPAP) provided by pressure generating device 4) is adjusted (e.g., by controller 22) to a different set of flow parameters to attempt to bring the patient's breath (i.e., patient breath data) into accordance with the target patient breath parameters previously calculated in step 112. Such adjustment may be carried out: gradually over a predetermined period of time (e.g., without limitation, a few minutes); gradually over a predetermined number of breaths (e.g., without limitation 10 breaths); abruptly; or via any other timing or event arrangement (e.g., without limitation, receiving a signal from an external sensor that the patient is asleep).

After the flow of breathing gas has been adjusted to the different set of flow parameters, the patient's breathing is monitored so as to obtain new breath data, such as show at step 115. If from such monitoring it is determined, at step 116, that the new patient breath data accords with the target patient breathing parameters, the method moves on to step 117, wherein the patient is continued to be provided with the flow of treatment gas in accordance with the different set of flow parameters. However, if at step 116 it is determined that the patient's breath data, as monitored at step 115, does not accord with the target patient breath parameters, the method returns to step 114 and the flow of treatment gas to the patient is adjusted to yet another different set of flow parameters to try to bring the patient's breathing into accord with the target patient breath parameters.

While the flow of breathing gas is continued to be provided to the patient in accordance with the different set of flow parameters, such as shown at step 117, the occurrence/presence of one or more stop "stop conditions" is monitored, such as shown at step 118. The flow of treatment gas in accordance with the different set of flow parameters is continued to be provided to the patient until it is determined, at step 120, that a stop condition has occurred. As used herein, the term "stop condition", refers to any condition which indicates that pressure generating device 4 is to cease operating in hyper-ventilation mode and either return to the operating mode prior to hyper-ventilation mode (i.e., provide the flow of treatment gas in accordance with the first set of flow parameters) or to power off. For example, in order to avoid causing a central apnea in the patient, the patient's breath tail could be monitored. If the breath tail exceeds a predetermined length of time (e.g., 8 seconds) a stop condition could be indicated and pressure generating device would discontinue hyper-ventilation mode and return to normal operation. Other examples of such stop conditions include, without limitation, a breathing instability (e.g., variable breathing, dysnchronous breaths) and changes in lung compliance (LC) which would potentially indicate that the patient is fighting treatment, and an indication that the treatment is disturbing the patient (e.g., causing restlessness, etc.). In the case of LC, as LC is the ratio of tidal volume to pressure support (i.e. IPAP-EPAP), as the IPAP is increased to achieve the target breath parameters (e.g. tidal volume) the ratio of tidal volume to pressure support is monitored. If this ratio starts to change (e.g. decrease) it means that the tidal volume that is achieved with a given amount of pressure support has decreased (i.e. the patient's body is resisting what the device is trying to do) which could be a sign that the patient is fighting the device or could be a sign that the patient's lungs are over-inflated. In addition to the aforementioned conditions, the passage of a predetermined amount of time could signify a stop event. For example, it may be desirable for a patient to only receive hyper-ventilation treatment for a portion of the time that a CPAP treatment is provided.

Once it has been determined at step 120 that a stop condition has occurred (and not a power off indication), hyper-ventilation mode ceases and the flow of treatment gas is provided to the patient in accordance with the first set of parameters (e.g., default CPAP mode), such as shown at step 122. Such transition from hyper-ventilation mode back to the first set of parameters may be abrupt (e.g., in an emergency) or may be gradual (e.g., to not disrupt a patient's sleep). The flow of breathing gas is provided in accordance with the first set of parameters until it is determined at step 124 that the stop condition previously determined at step 120 has ceased. Then, at step 126, if it is determined that the patient has once again achieved stable breathing, method 100 returns to step 117 and the patient is once again provided with the flow of breathing gas in accordance with the different set of flow parameters. However, if it is determined at step 126 that the patient has not achieved stable breathing, the flow of breathing gas is continued to be supplied in accordance with the first set of parameters.

From the foregoing description it is to be appreciated that the present invention provides for the combined treatment of both OSA and hypertension with a single respiratory therapy mode. It is also to be appreciated that such approach ensures that patient physiology is not adversely affected by lung-hyperventilation and ensures that patient comfort is maintained.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for the concurrent treatment of obstructive sleep apnea and hypertension in a patient, the method comprising:
   providing a flow of treatment gas to the airway of the patient in accordance with a first set of flow parameters;
   determining that the patient has achieved stable breathing while receiving the provided flow of treatment gas in accordance with the first set of flow parameters;
   collecting breath data of the patient while receiving the flow of treatment gas in accordance with the first set of flow parameters;
   determining a set of target patient breath parameters from the breath data;
   adjusting the flow of treatment gas to a different set of flow parameters;

monitoring the patient to obtain new patient breath data;
determining that the new patient breath data accords with the target patient breath parameters;
providing the flow of treatment gas to the patient in accordance with the different set of flow parameters as a hyper-ventilation mode, wherein the target patient breath parameters include a target tidal volume of the patient which is greater than a first tidal volume of the patient; and
determining that a stop condition has occurred during the hyper-ventilation mode, and responsive thereto, providing the flow of breathing gas in accordance with the first set of flow parameters.

2. The method of claim 1, wherein the target tidal volume is in the range of about 150% to about 400% of the first tidal volume.

3. The method of claim 2, wherein determining that the patient has achieved stable breathing comprises determining that at least one of a minute ventilation, a breath rate, or a tidal volume of the patient is consistent.

4. The method of claim 2, wherein collecting breath data comprises determining at least one of a minute ventilation, a breath rate, or a tidal volume of the patient.

5. The method of claim 2, wherein adjusting the flow of treatment gas to bring the patient breath data into accordance with the target patient breath parameters is carried out gradually over a predetermined period of time.

6. The method of claim 2, wherein adjusting the flow of treatment gas to bring the patient breath data into accordance with the target patient breath parameters is carried out over a predetermined quantity of breaths by the patient.

7. A gas flow generator having a controller which is programmed to carry out the method of claim 1.

8. A machine readable memory having instructions encoded therein for carrying out the method of claim 1.

9. The method of claim 1, wherein determining that a stop condition has occurred comprises at least one selected from the group consisting of:
determining that a breath tail of the patient exceeds a predetermined length of time,
determining that a breathing instability has occurred,
determining a change in lung compliance, and
determining that a predetermined amount of time has passed.

10. The method of claim 1, further comprising:
determining that the stop condition has ceased;
determining that the patient has achieved stable breathing; and
again providing the flow of treatment gas to the patient in accordance with the different set of flow parameters.

11. A method for the concurrent treatment of obstructive sleep apnea and hypertension in a patient, the method comprising:
providing a flow of treatment gas to the airway of the patient in accordance with a first set of flow parameters;
determining that the patient has achieved stable breathing while receiving the provided flow of treatment gas in accordance with the first set of flow parameters;
collecting breath data of the patient while receiving the flow of treatment gas in accordance with the first set of flow parameters;
determining a set of target patient breath parameters from the breath data;
adjusting the flow of treatment gas to a different set of flow parameters;
monitoring the patient to obtain new patient breath data;
determining that the new patient breath data accords with the target patient breath parameters;
providing the flow of treatment gas to the patient in accordance with the different set of flow parameters as a hyper-ventilation mode, wherein the target patient breath parameters include a target tidal volume of the patient which is greater than a first tidal volume of the patient, wherein the target tidal volume is in the range of about 150% to about 400% of the first tidal volume; and
determining that a stop condition has occurred during the hyper-ventilation mode, and responsive thereto, providing the flow of breathing gas in accordance with the first set of flow parameters.

12. The method of claim 11, wherein determining that a stop condition has occurred comprises determining that a breath tail of the patient exceeds a predetermined length of time.

13. The method of claim 11, wherein determining that a stop condition has occurred comprises determining that a breathing instability has occurred.

14. The method of claim 11, wherein determining that a stop condition has occurred comprises determining a change in lung compliance.

15. The method of claim 11, wherein determining that a stop condition has occurred comprises determining that a predetermined amount of time has passed.

16. The method of claim 11, further comprising:
determining that the stop condition has ceased;
determining that the patient has achieved stable breathing; and
again providing the flow of treatment gas to the patient in accordance with the different set of flow parameters.

17. The method of claim 11, wherein determining that the patient has achieved stable breathing comprises determining that at least one of a minute ventilation, a breath rate, or a tidal volume of the patient is consistent.

18. The method of claim 11, wherein collecting breath data comprises determining at least one of a minute ventilation, a breath rate, or a tidal volume of the patient.

19. The method of claim 11, wherein adjusting the flow of treatment gas to bring the patient breath data into accordance with the target patient breath parameters is carried out gradually over a predetermined period of time.

20. The method of claim 11, wherein adjusting the flow of treatment gas to bring the patient breath data into accordance with the target patient breath parameters is carried out over a predetermined quantity of breaths by the patient.

* * * * *